US011140904B2

(12) United States Patent
Fokin et al.

(10) Patent No.: US 11,140,904 B2
(45) Date of Patent: Oct. 12, 2021

(54) BIOLOGICALLY ACTIVE PREPARATION FOR PROTECTING PLANTS AGAINST PESTS, METHOD FOR PRODUCING SAME, MICROCONTAINER FOR SAID PREPARATION, METHOD FOR MANUFACTURING SAME, AND METHOD OF PROTECTING PLANTS AGAINST PESTS

(71) Applicant: OBSHCHESTVO S OGRANITCHENNOY OTVETSTVENNOST'YU "FUNGIPAK", Alabino (RU)

(72) Inventors: Oleg Viktorovitch Fokin, Moscovskaya oblast' (RU); Viktor Vladimirovitch Seregin, Moscovskaya oblast' (RU)

(73) Assignee: OBSHCHESTVO S OGRANITCHENNOY OTVETSTVENNOST'YU "FUNGIPAK", Alabino (RU)

( * ) Notice: Subject to any disclaimer, the term of this patent is extended or adjusted under 35 U.S.C. 154(b) by 173 days.

(21) Appl. No.: 15/751,608

(22) PCT Filed: Aug. 17, 2015

(86) PCT No.: PCT/RU2015/000516
§ 371 (c)(1),
(2) Date: Feb. 9, 2018

(87) PCT Pub. No.: WO2017/030457
PCT Pub. Date: Feb. 23, 2017

(65) Prior Publication Data
US 2019/0261635 A1    Aug. 29, 2019

(51) Int. Cl.
*A01N 63/30* (2020.01)
*C12N 1/14* (2006.01)
*B01J 13/14* (2006.01)
*B01J 13/20* (2006.01)

(52) U.S. Cl.
CPC .............. *A01N 63/30* (2020.01); *B01J 13/14* (2013.01); *B01J 13/206* (2013.01); *C12N 1/14* (2013.01)

(58) Field of Classification Search
None
See application file for complete search history.

(56) References Cited

U.S. PATENT DOCUMENTS 4,724,147 A * 2/1988 Marois ............... C12N 3/00
424/93.5

FOREIGN PATENT DOCUMENTS

| GB | 2 214 080 A | 8/1989 |
| RU | 2 483 540 C2 | 6/2013 |
| RU | 2 487 542 C2 | 7/2013 |
| WO | WO 90/02655 A1 | 3/1990 |

OTHER PUBLICATIONS

Park et al (Enzyme and Microbial Technology 26:235-242, 2000).*
Bajpai et al (Advanced Functional Materials, 14(2):145-151, 2004).*
Zhang et al (BioOne Complete/ Journal of Orthoptera Research 14(1):27-30, 2005).*
Canadian Office Action dated Oct. 15, 2018 in Patent Application No. 2,988,312, 4 pages.
International Search Report and Written Opinion dated May 26, 2016 in PCT/RU2015/000516 filed Aug. 17, 2015.
Jaroslav Weiser, "The Microbiological Methods for Insect Pest Control (Diseases of Insects)", 1972, 4 total pages (with English translation).
Chinese Office Action dated Jan. 19, 2020 in Chinese Patent Application No. 201580080261.1 (with English translation), citing documents AO and AX therein, 11 pages.
Zhao, J., "Research and development of Beauveria bassiana microcapsule", Agricultural Science and Technology series of China Excellent Master's Degree Thesis full text database, issue 7; Jul. 15, 2010; pp. D046-123.

* cited by examiner

*Primary Examiner* — Patricia Duffy
(74) *Attorney, Agent, or Firm* — Oblon, McClelland, Maier & Neustadt, L.L.P.

(57) ABSTRACT

The invention relates to the field of protecting plants against pests, and more particularly to a method of protecting plants against pests, which can be used for industrial and scientific purposes, in agriculture, horticulture and forestry. The method of protecting plants against pests according to the present invention comprises applying a biologically active preparation pre-activated in an aqueous medium to a plant, the preparation comprising microcontainers and a biological insecticide, wherein the microcontainers are made from a polymeric material in the form of a hollow receptacle with at least one opening, via which the biological insecticide is placed inside the microcontainers. The invention also provides a microcontainer and a preparation for realisation of the stated method. Furthermore, the invention provides methods for producing a microcontainer and the aforementioned preparation.

9 Claims, 16 Drawing Sheets

BIOLOGICALLY ACTIVE PREPARATION FOR PROTECTING PLANTS AGAINST PESTS, METHOD FOR PRODUCING SAME, MICROCONTAINER FOR SAID PREPARATION, METHOD FOR MANUFACTURING SAME, AND METHOD OF PROTECTING PLANTS AGAINST PESTS

TECHNICAL FIELD OF INVENTION

The present invention relates to the field crop protection against insect pests and may be useful in industry, scientific research, agriculture, gardening and forestry. In particular, the proposed invention offers a method for crop protection against insect pests by means of the treatment of crops to be protected with a biologically active agent, wherein an insecticide is placed into a protective microcontainer. The invention also offers the above-indicated biologically active agent and a microcontainer in addition to methods of the production and manufacture of the same.

BACKGROUND ART

Large-scale use of pesticides has a number of fundamental disadvantages. The key disadvantages include a growth of hard-to-kill population of insect pests and contamination of the environment. In addition, a long-term struggle with the locusts demonstrates that insecticides tend to ensure only a temporary reduction of insect pest populations and mitigation of pest-related harm to crops within areas of insecticidal agent use. But, in general, such insecticides being used are hardly able to radically control the longstanding dynamics of insect pest population growth. On the contrary, large-scale insecticidal treatments do a lot of harm to environmental situation as a result of elimination of natural enemy populations and natural epizooties, thus increasing mass pest reproduction period by several years.

One of the methods for suppression of harmful phytophags is a microbiological protection method.

Formulations based on entomopathogenic microorganisms are well known from the prior art and they are widely used worldwide to control the locust populations. Unlike tough chemical insecticides doing irreparable harm to ecological systems and prohibited under national laws for use within water and wild nature preserving areas, biological insecticides relate to agents harmless to recreational and water conservation zones, safe for warm-blooded animal subjects, including human subjects, and they may be used at locations where environmentally pure food products are made.

The above-indicated problems are widely discussed in numerous publications such as J. "Agrochemistry", 2010, No.12, p. 24-28, "The effect of fillers upon biological effectiveness of a biomass of conidia entomopatogenic fungus *Beauveria bassiana* used against the locusts under conditions existing in Kazakhstan" by V. Ju. Ktukov at al.; published work by Lomer C. J., Bateman R. P., Johnson D. L, Lagewald J., Thomas M. Biological control of locusts and grasshoppers // Annu. Rev. Entomol. 2001. V. 46. P. 667-702, and by Charnley A. K., Collins S. A. Entomopathogenic fungi and their role in pest control // Environmental and microbial relationships. The Mycota: A comprehensive treatise on fungi as experimental systems for basic and applied research/Eds. C P. Kubicek, K. Esser and I. S. Druzhinina. Springer, 2007. P. 159-187; published work by Lachininsky A. V., Sergeeva M. G., Childebayev M. K, Chernyakhovsky M. E., Lockwood J. A., Kambulin V. E., Gaplarova F. A. "The locusts of Kazakhstan, Middle Asia and adjacent territories", Larami: MAPA and University of Wyoming, 2002, 387 pages.

However, use of entomopathogenic microorganisms against locust populations faces a number of problems related to unstable effect they produce. First of all, said problems are associated with such limiting factors of arid climate as solar radiation, high temperature and low air humidity. It has been known that in the event of exposure to direct sunlight fungal condia tend to lose their viability in several hours and such viability loss results in substantial decrease in the effectiveness of mycoinsecticidal biological agents. This particular point is addressed in the following publications: Gromovykh T. И. "The entomopathogenic fungi in the protection of forests", Novisibirsk: Nauka, 1982., Inglis G. D., Johnson D. L, Goettel M. S. "Effects of temperature and sunlight on mycosis (*Beauveria bassiana*) (Hyphomycetes: Sympodulosporae) of grasshoppers under field conditions // Environ. Entomol 1997. V. 26. P. 400-409, Braga G. U. L Flint S. D., Messias C. L., Anderson A. J., Roberts D. W. Effect of UV-B on conidia and germlings of the entomopathogenic hyphomycete *Metarhizium anisopiiae* // Mycol. Res. 2001. V. 105. V. 105. No. 7. P. 874-882, Braga G. U. L., Flint S. D., Miller C D., Anderson A. J., Roberts D. W. Variability in response to UV-B among species and strains of *Metarhizium* isolated from sites at latitudes from 61° N to 54° S // J. Invertebr. Pathol. 2001. V. 78 P. 98-108, Wraight S. P., Inglis G. D., Goettel M. S. Fungi// Field manual of techniques in invertebrate pathology. Application and evaluation of pathogens for control of insects and other invertebrate pests. Springer, 2007. P. 223-248.

Therefore, a search for protector fillers for entomopathogenic microorganisms seems to be a topical issue. Several researches demonstrate that promising fillers of the kind are clays, humates, activated carbon, titanium dioxide, zinc oxide, fluorescent decolourants (Tinopal L P W, Blankophor B S U), vegetable and mineral oils, molasses, dehydrated milk, egg albumin and some others. For example, see the following publications: Inglis G. D., Goettel M. S., Johnson D. L Influence of ultraviolet light protectants on persistence of the entomopathogenic fungus *Beauveria bassiana* // Biol. Contr. 1995. V 5. No. 4. P. 581-590, Edgington S., Segura H., de La Rosa W., Williams T. Photoprotection of *Beauveria bassiana:* testing simple formulations for control of the coffee berry borer// Int. J. Pest Manag. 2000. V. 46. No 3. P. 169-176; Kassa A. Development and testing of mycoinsecticides based on submerged spores and aerial conidia of the ento-mopathogenic fungi *Beauveria bassiana* and *Metarhizium anisopliae* (Deuteromycotina: Hyphomycetes) for control of locusts, grasshoppers and storage pests. Doctoral diss. GOttingen: Georg-August-University, 2003. 170 p.; Inglis G. D., Goettel M. S., Eriandson M. A., Weaver D. K. Grasshoppers and locusts // Field manual of techniques in invertebrate pathology. Application and evaluation of pathogens for control of insects and other invertebrate pests. Springer, 2007. P. 627-654.

These protectors may differ in terms of their effectiveness depending of types of micromycetes, target subjects and their habitat.

As shown in the above-referenced prior art published sources, in terms of locust population control, a most promising group out of the existing multitude of entomopathogenic organisms includes fungi of anamorphic species *Metarhizium* and *Beauveria.* As a result of research work, two preparations on the basis of fungus *Metarhizium anisopliae* var. *acridum* under trade names Green Muscle®

(Republic of South Africa) and Green Guard® (Australia) were created and implemented successfully. These preparations showed high biological effectiveness (85-95%) against the migratory locusts, desert locusts, *Moroccan locusts* and grasshoppers. Based on *B. Bassiana,* two experimental anti-locust agent had been created in the U.S.A. under trade names Mycocide GH® and Mycotrol®. K. However, tests of such agents carried out in the ex-US SR's territories showed their low effectiveness under climate conditions of the former USSR' republics. Analysis of these agents showed that they are extremely sensitive to UV radiation, temperature and humidity of the surrounding environment. The suggested methods of the anti-pest treatment of agricultural lands using above-said agents as components of oil-water suspensions with fillers such as humate, clay, molasses and some others widely used fillers do not contribute much to the results of treatment and, simultaneously, they block the possibility of using such agents in case of ultra small-volume spraying.

The present invention is directed to further development of protector fillers for entomopathogenic microorganisms, wherein the above-indicated development is intended to be performed in a quite different manner unparalleled in the prior art. The technical solution suggested by the present invention enables to minimize adverse effect produced on the part of negative factors upon the viability of active agent of biological insecticides, in particular upon the viability of entomopathogenic microorganisms, enhance both consumer and commercial properties of biologically active agents in the event of their mass use, broaden the field of use of biological insecticides up to ultra small-volume spraying.

DISCLOSURE OF THE INVENTION

The present invention offers a method for producing a biologically active agent for crop protection against insect pests, the method comprising the steps of introducing a biologically active suspension comprising fungal spores and a liquid phase into microcontainers, decanting subsequently the liquid phase, and drying said microcontainers containing fungal spores.

As fungal material, entomopathogenic fungi may be used, in particular entomopathogenic fungus selected from the group consisting of fungal species *Beauveria bassiana, Pandora neoaphidis, Entomophaga maimaiga, Metharhizium anisopliae* var. *acridium* and *Metharhizium anisopliae* var. *anisopliae* and, more preferably, entomopathogenic fungus of fungal species *Metharhizium anisopliae* var. *acridium.*

The above-indicated microcontainer may receive from 1 to 100 of fungal spores. In addition, the present invention suggest a biologically active agent for the crop protection against insect pests and plant diseases, which is produced by the above-indicated method, and also a method for manufacturing a microcontainer to implement the above-indicated method, according to which microcapsules having a polymeric material shell and an organic solvent core are produced, then said microcapsules are heated up to 300° C. to cause a perforation of the microcapsule shell and formation of holes therein as a result of action of solvent vapour pressure, wherein a size of said microcapsule shell holes is adjustable my means of a proportion of polymeric material components for said shell and varying said solvent vapour pressure.

In the above-said method for manufacturing a microcontainer, the microcapsules may be produced to be of a size ranging from 5 to 500 µm.

Thiourea may be used as said polymeric material.

The shell thickness is selected such that to be within a range from 0.05 to 5 µm.

The size of said holes is adjustable up to a diameter of at least 5 µm.

The present invention also covers a structure of the microcontainer manufactured by means of the claimed method for manufacturing a microcontainer, and covers a method for the crop protection against insect pests, comprising the steps of activating a biologically active agent of claim 6 in an aqueous medium and applying said agent onto crops to be protected.

The present invention rests on the basic idea of using a microcontainer with "programmable properties" as a protector filler for bioinsecticide, the microcontainer being made of synthetic polymer shaped as a hollow receptacle having at least one hole to receive fungal spores. Such microcontainer has the following advantages over known fillers:

1. Dispersiveness—microcontainer size ranges from 1 to 500 µm. It can be preset in the microcontainer production. Protector filler grinding is not required. Versatility for various sorts of fungal spores.

2. Diameter of holes to made in the shell of protector filler can be set in the microcontainer production to receive spores of various sizes. Versatility for various sorts of fungal spores.

3. Non-reactive polymer of the shell of protector filler, which is friendly to fungal spores and surrounding environment.

4. Biodegradable polymer of the shell of protector filler, which assists in maintaining environmental safety.

5. Polymer of the shell of protector filler offers the protection against solar radiation.

6. Polymer of the shell of protector filler does not virtually changes its properties within temperature range from −20° C. to +50° C. and microcontainer properties are not subject to change under the same conditions.

7. Polymer of protector filler is insoluble in water and not swellable.

A microcontainer according to the present invention fully protects the bioinsecticide contained therein from harmful UV radiation, maintains necessary humidity level on the inside to ensure existence of microorganisms, safeguards the microorganisms from high temperatures, has a prolonged, preset operating time and offers fair "sticky" properties. The microcontainer size may be agreed with major manufacturers of equipment for ultra small-volume spraying.

Ultra small-volume spraying is a sort of small-drop spraying with pesticide (i.e. at least 80% of pesticidal agent is sprayed in the form of drops sizing from 50 to 150 µm) to cover a surface to be treated, wherein rated consumption of the pesticide is up to 5.0 liter per hectare. Ultra small-volume spraying provides for a due penetration of the pesticidal agent into inter-row spacing of thick planting areas, a highly dense coverage of plants, including a lower portion of leaves, thus enabling to reduce a consumption of an agent being sprayed by at least 20-30%, as compared to other spraying techniques.

Use of chemical insecticides is either limited or prohibited under national laws within water and wild nature preserving areas where a growth of the locust populations takes place. Therefore, providing a fundamentally novel and safe biologically active agent enables to hugely increase areas to be treated and, as a result, timely prevent lethal attacks of very dangerous pests on agricultural lands.

As opposed to what is known from the prior art, the present invention sets up a new trend of developing filler protectors for biological insecticides. It suggests putting a bioinsecticidal agent inside a microcontainer so that said agent can be protected effectively from adverse environmental effects and further released controllably from the microcontainer. Technical solution suggested by the present invention allows to achieve the following:

1. A 3.8-4.2 fold decrease in exposure of fungal spores to UV radiation owing to placing said fungal spores within a microcontainer for being held inside as a temporary stored component, not as a mixture with a filler or a coat onto a filler. In the latter case, there is less intense effect of UV radiation, for example in water-oil solution, due to lesser evaporation rate, while in the former case there is a protection of fungal conidia by microcontainer wall from solar radiation, thus providing for most favourable conditions for fungal conidia existence.

2. A mitigation of effect produced by high temperature, e.g. on a surface of soil or plants. As shown above, a number of authors that refer to conidia of entomopathogenic fungi as an example prove that a temperature rise kills said fungal conidia before onset of the desired effect. Placement of bioinsecticidal agent inside a microcontainer is similar to placing the same into a thermos bottle and such option is capable of preventing overheating of active agent. While using of a microcontainer, an outer temperature ranging from 60-70° C. is not critical for microorganisms and elimination of sprouted conidia of fungi on a surface of the microcontainer is not critical as well for effectiveness of treatment by the agent.

3. A mitigation of effect produced by humidity. When sun is highly active and surrounding conditions are very hot, an intensive evaporation of moisture necessary for normal existence of bioinsecticides occurs. As a result of overdrying, fungal conidia perform a transition to sporous inactive phase with a loss of bioinsecticidal properties. When it comes to fungal conidia held inside a microcontainer after being soaked in a liquid, as suggested by the present invention, the claimed technical solution provides for perfect conditions for the growth of microorganisms inside the microcontainer and for a controllable release of fungal micro-spores coming to a surface the microcontainer. When insect pests contact a surface of microcontainer, they get infected with spores of entomopathogenic fungi. Due to preset release rate responsible for delivery of fungal conidia to microcontainer surface, a biologically active agent as per the present invention, by contrast to commonly used insecticidal agents known from the prior art, offers a prolonged effect lasting for several days, while known chemical and biological insecticides remain active only for several hours or, at best, for the first 24 hours after the insecticidal treatment. This particular feature allows to use the inventive biological agents without strict observance of time limits for the treatment.

4. An improvement of adhesive properties of biologically active agents for the crop protection from insect pests by means of imparting special properties to microcontainer walls. Thus, laboratory tests show that this particular preparative form is much more resistant to wind and moisture as compared to commonly used preparative forms. When applied to a surface of soil or plant being treated, the inventive agent does not fall down, but reliably adheres to the surface and, in case of being eaten by an insect pest, it tends to cause fungal spores to grow inside the insect pest body.

5. A greater weight of a biologically active agent for the crop protection from insect pests as compared to weight of an active substance of said agent (e.g. fungal conidia), making it possible to avoid "foggy" effect over the area being exposed to aerial treatment and preset necessary size of the microcontainer (ranging from 5 to 500 µm), which ensures undeniable benefit when it comes to use of the inventive agent for ultra small-volume spraying technique basing on minimal consumption of a liquid, as it may be particularly necessary under arid and desert climatic conditions.

6. Non-use of commonly applied technology of conidial mass production by means two-phase cultivation technique, when submerged cultivation for several days is carried out first, followed by applying inoculum on a surface carrier for the production of fungal biomass for several weeks. The methods suggested by the present invention allow to no longer use of submerged cultivation requiring large areas, substantial power and labour consumption.

The methods as per the present invention make it possible to load conidial mass of the fungus from a reactor (a fermenter) directly into a microcontainer, thus leading to significant increase of active substance concentration inside the microcontainer as compared to initial concentration of active substance in a solution.

BRIEF DESCRIPTION OF DRAWINGS

FIG. 5 shows a diameter of microcontainer hole (44.30 µm) and diameters of fungal conidia (4.59 µm and 4.21 µm). FIG. 6 uses arrows to mark fungal conidia.

EMBODIMENTS OF CLAIMED INVENTION

Figure 1:
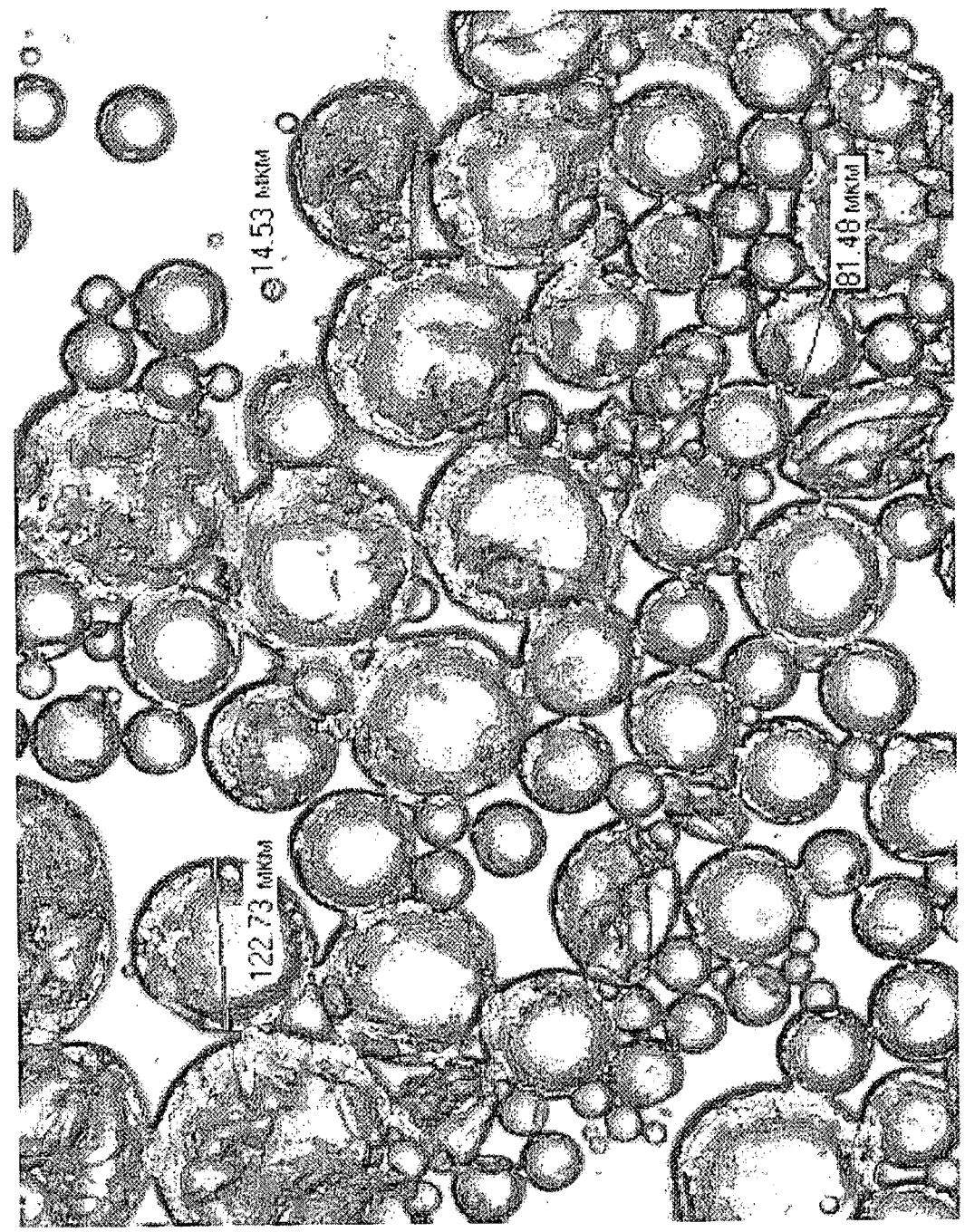
FIG. 1 shows hollow receptacles filled with an organic solvent, i.e. microcapsules. Such microcapsules are made of thiourea material and xylol is used as said organic solvent. Diameters of microcapsules are indicated (14.53 µm, 81.48 µmи 122.73 µm) on this figure.
Figure 2:
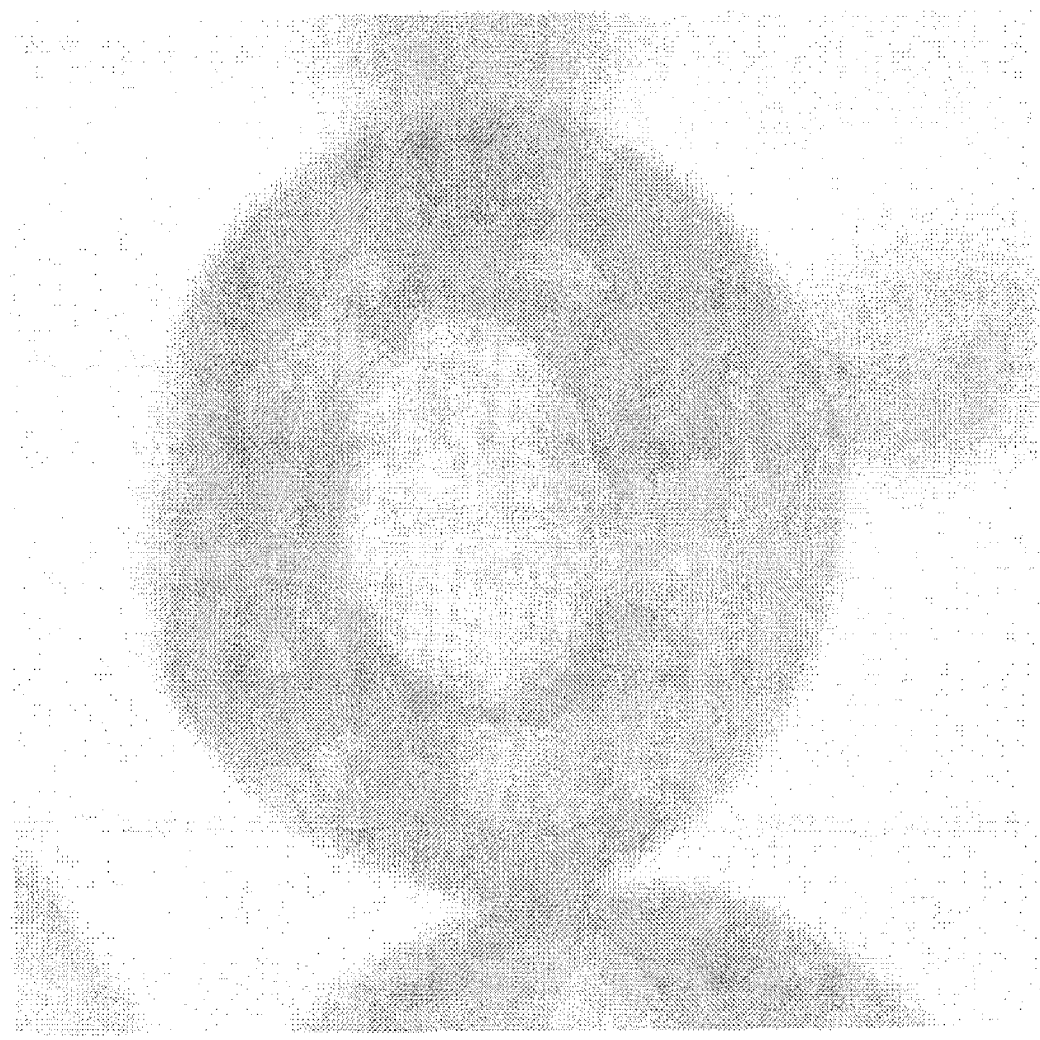
FIG. 2-3 show hollow receptacles having at least one hole, i.e. microcontainers to receive a fluid. Water is used as said fluid.
Figure 3:
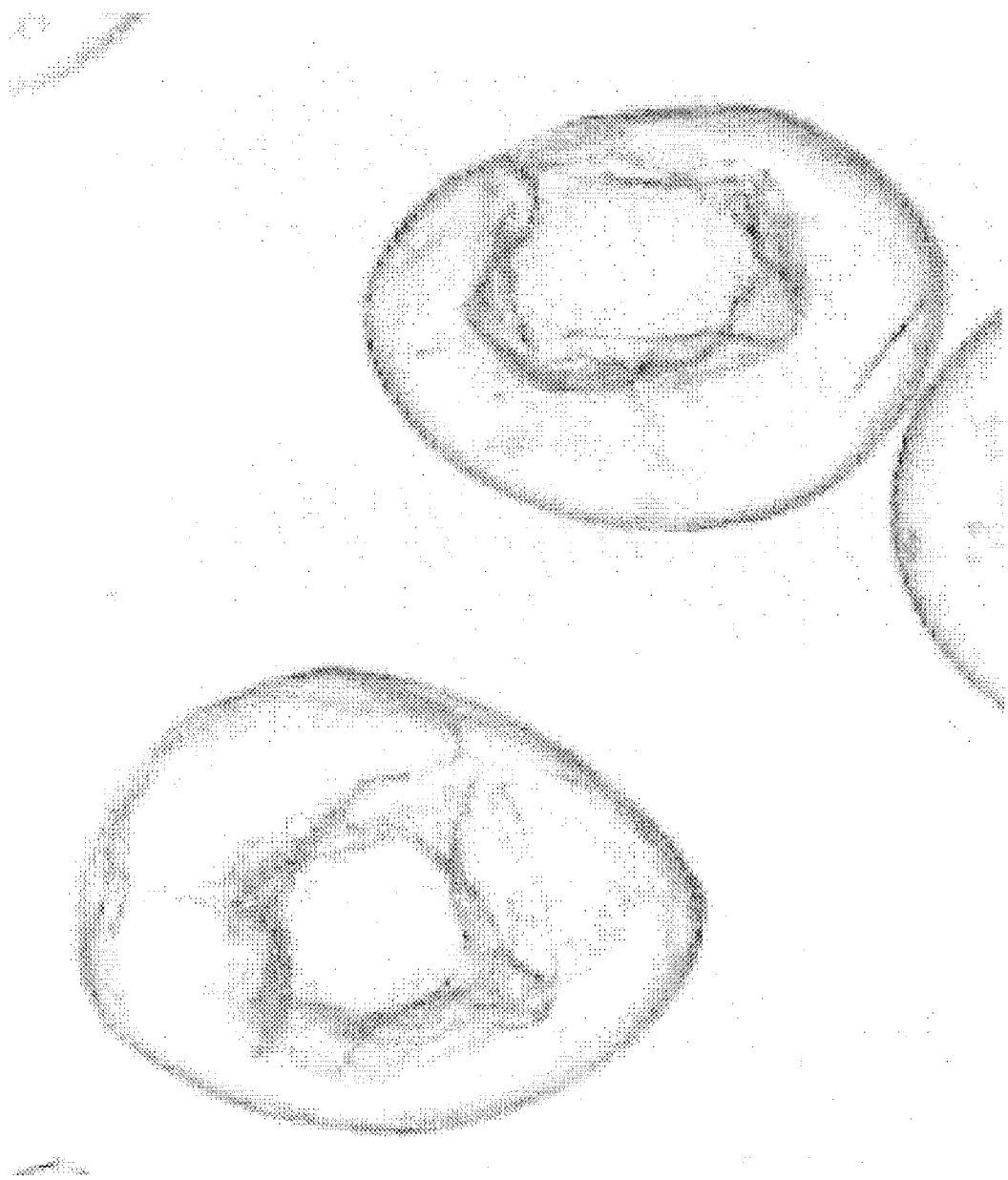
Figure 4:
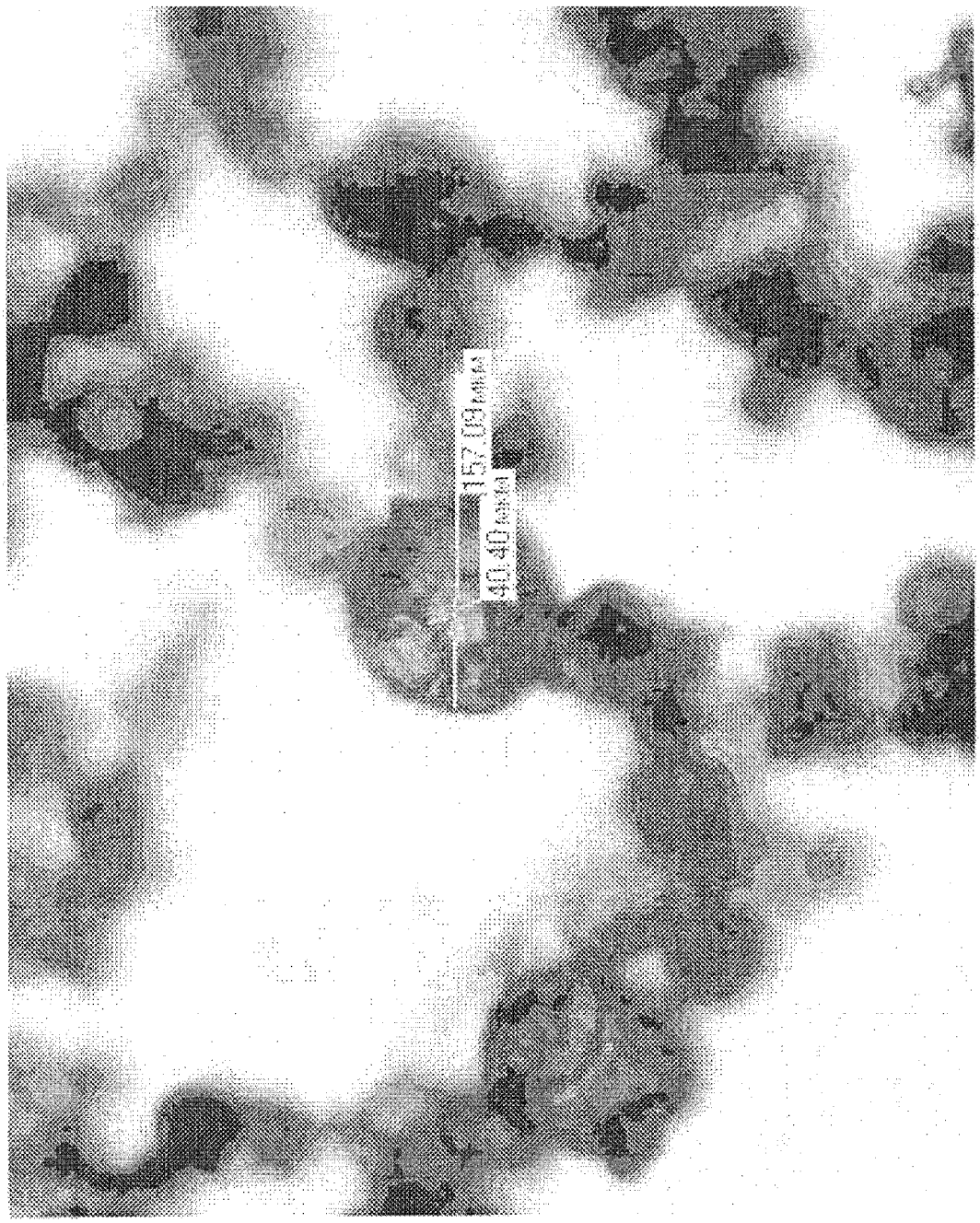
FIG. 4 shows microcontainers in a liquid phase under 100-fold magnification. Microcontainer diameter (157.09 µm) and hole diameter (40.40 µm) are indicated on this particular figure.
Figure 5:
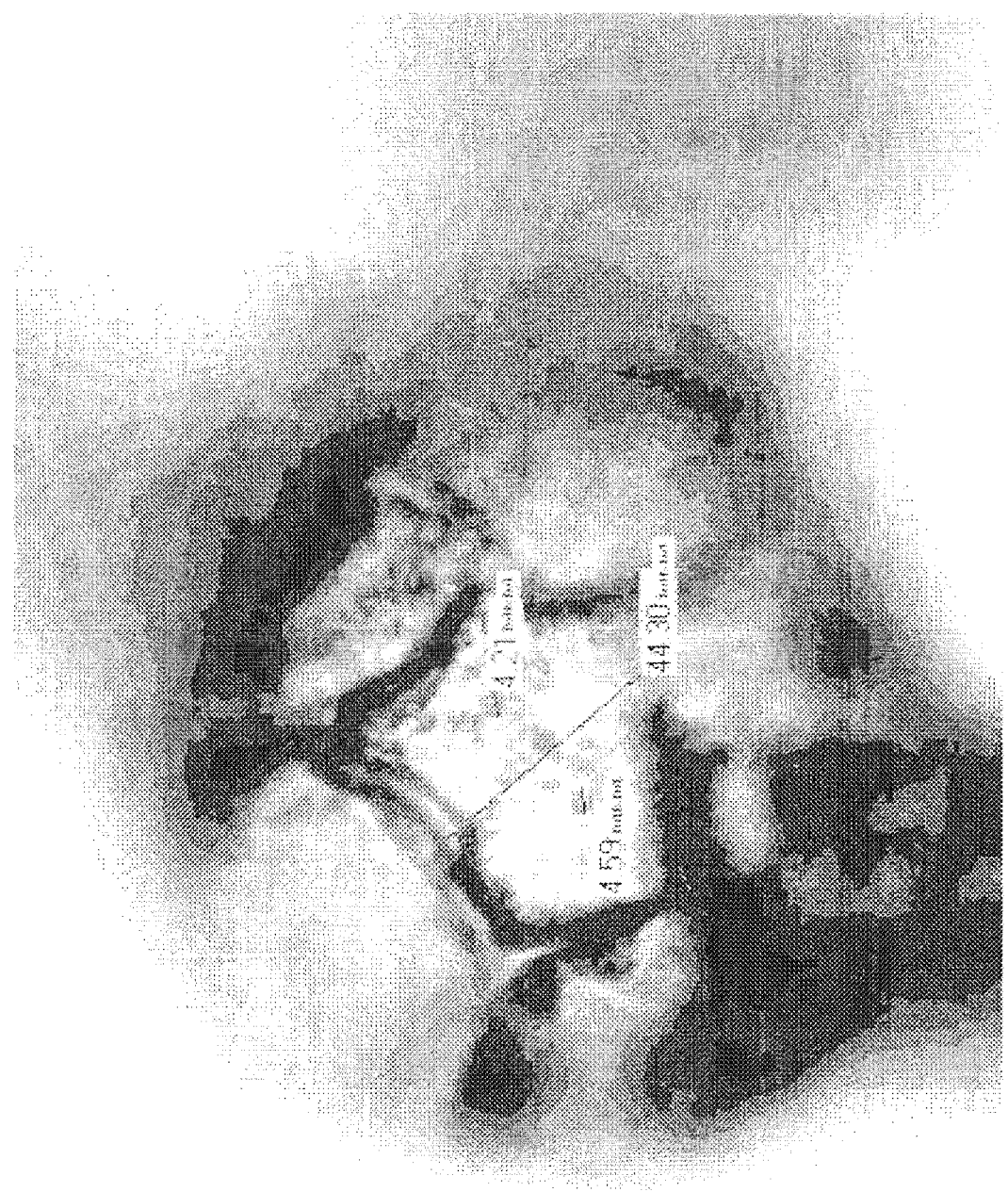
FIGS. 5-6 show microcontainers comprising fungal conidia under 400-fold magnification.
Figure 6:
Figure 7:
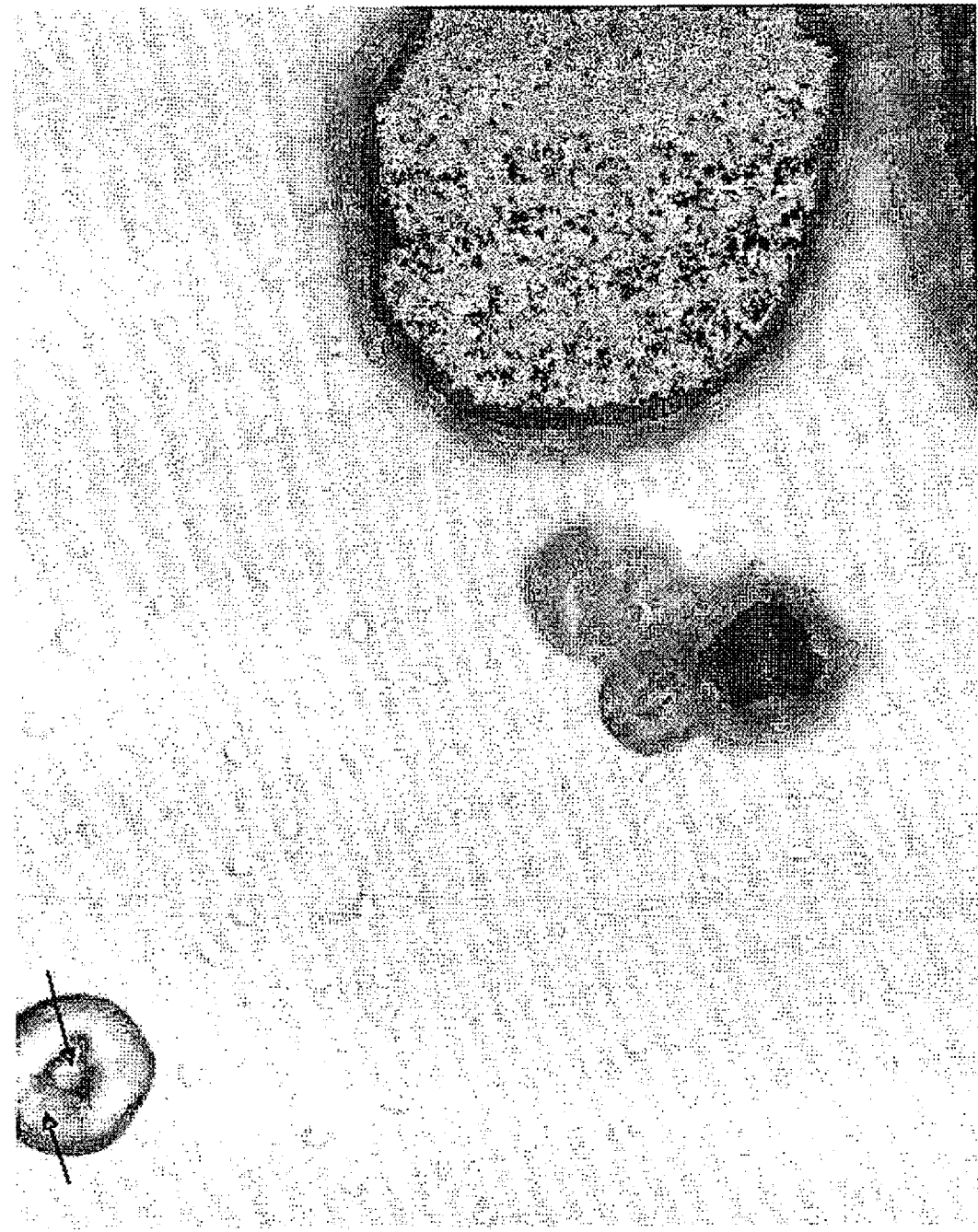
FIG. 7 shows microcontainers comprising fungal conidia (shown by arrows) placed to a liquid phase comprising fungal conidia.
Figure 8:
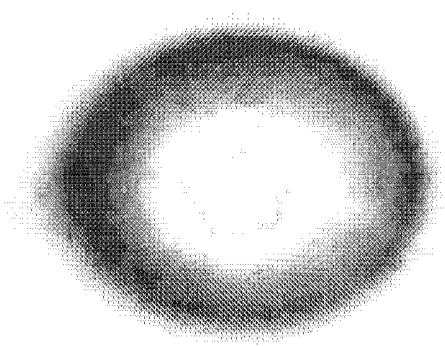
FIG. 8 shows a microcontainer with a hole.
Figure 9:
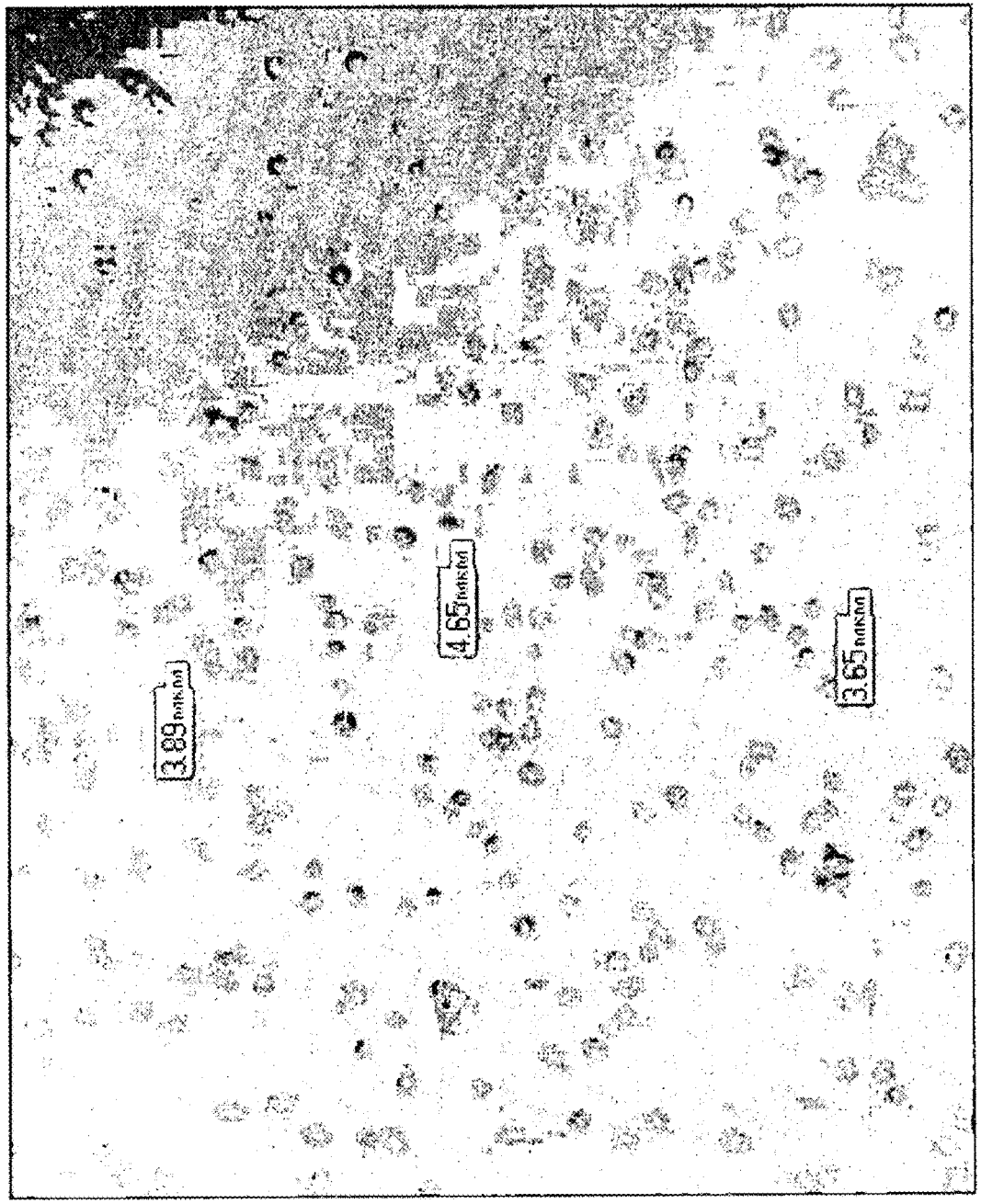
FIG. 9 shows spores of entonopathogenic fungi in a liquid phase. Spore diameter is 3.5 to 5 µm. Spore diameters (3.65 µm, 3.89 µm and 4.65 µm) are indicated on this particular figure.
Figure 10:
FIG. 10 shows microcontainers comprising fungal conidia placed to a liquid phase.
Figure 11:
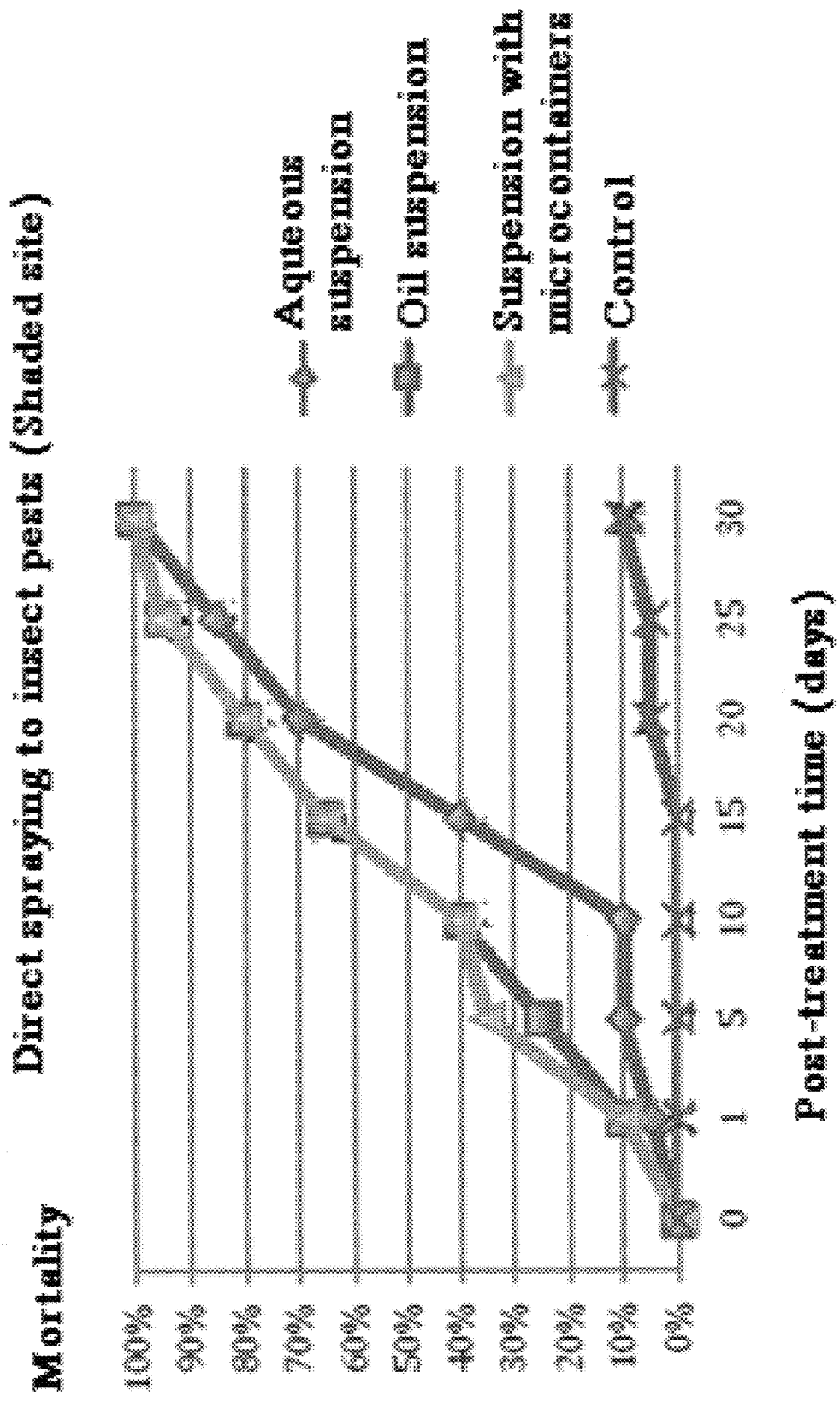
FIG. 11 shows a graph representing the mortality of locust larvae in case of using a mycoinsecticidal agent provided in various preparative forms. Preparative forms were used for pesticidal treatment of insect pests at shaded sites.
Figure 12:
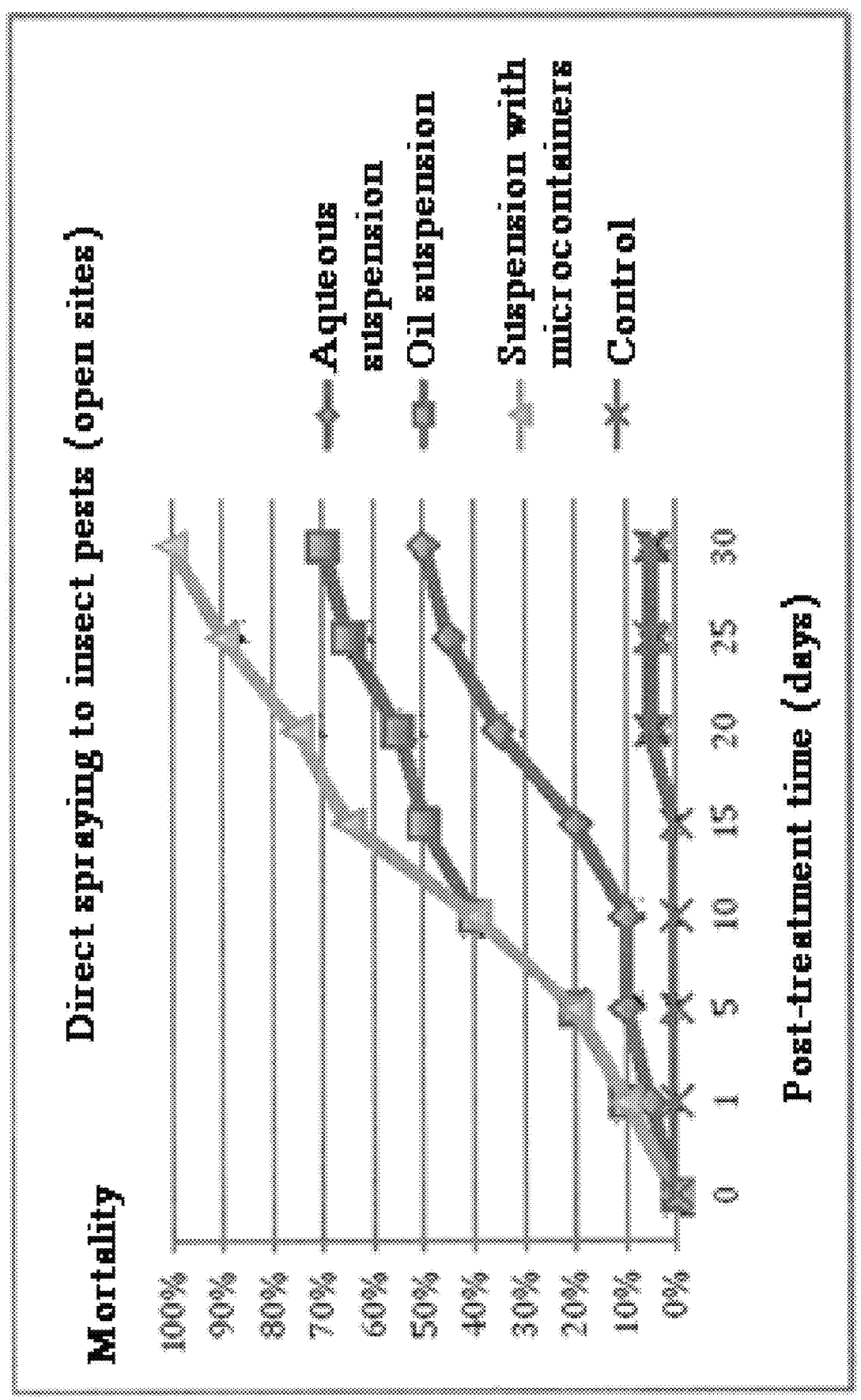
FIG. 12 shows a graph representing the mortality of locust larvae in case of using a mycoinsecticidal agent provided in various preparative forms. Preparative forms were used for pesticidal treatment of insect pests at open sites.
Figure 13:
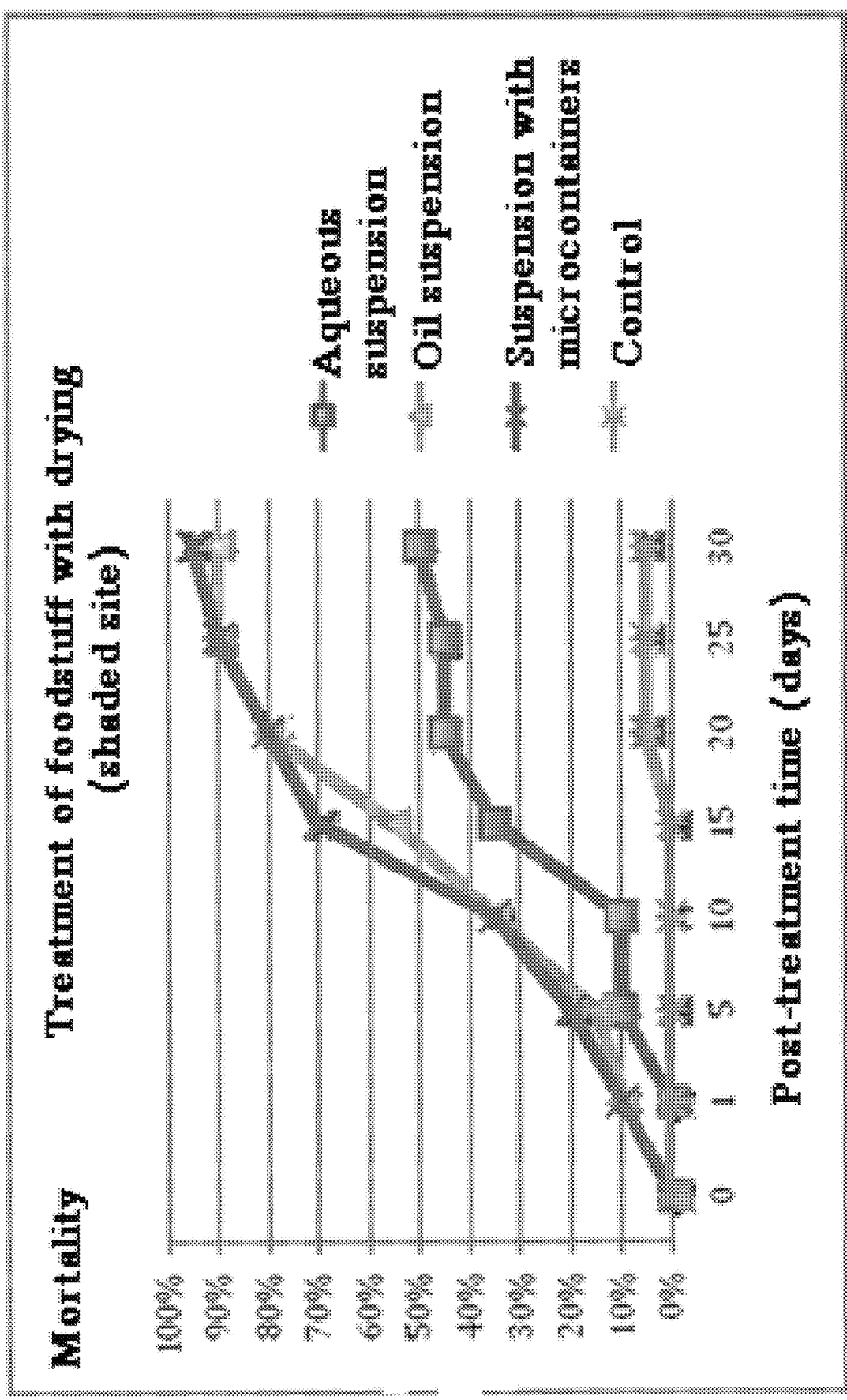
FIG. 13 shows a graph representing the mortality of locust larvae in case of using a mycoinsecticidal agent provided in various preparative forms. Preparative forms were used for the treatment of a foodstuff at shaded sites.
Figure 14:
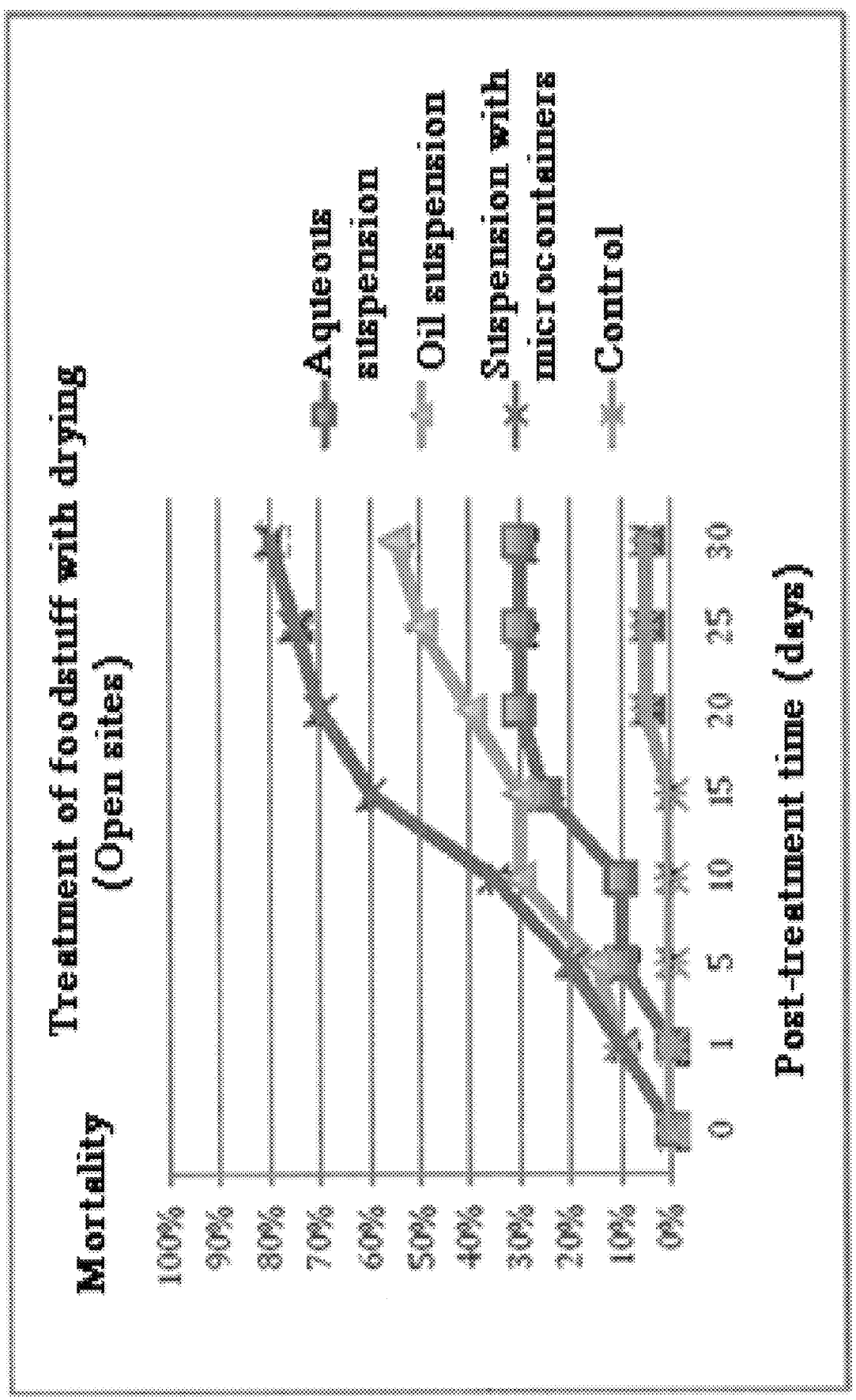
FIG. 14 shows a graph representing the mortality of locust larvae in case of using a mycoinsecticidal agent provided in various preparative forms. Preparative forms were used for the treatment of a foodstuff at open sites.

As mentioned above, a core of the claimed invention is providing a fundamentally new method for the production of a biologically active agent for the crop protection against insect pests, wherein an active substance of the biologically active agent is placed inside a microcontainer.

Therefore, a key means for realization of the above-identified inventive method for the production of a biologically active agent for the crop protection against insect pests includes microcontainers, and the present invention also offers a method for the manufacture of such microcontainers, a core of said method for the manufacture of microcontainers is use of micro-encapsulation technique in order to make special microcapsules that may be useful under a certain temperature for the manufacture of microcontainers due to perforation of a microcapsule shell to form holes extending though said shell.

The prior art knows methods for the production of a microcapsule comprising a solution of pyrethroid and organophosphoric insecticides in an organic solvent, and also methods for the production of a microcapsule comprising an organic solvent only. According to above-said methods known from the prior art, a solution of in secticide or an organic solvent is mixed with polyfunctional isocyanate, wherein said insecticide is stirred till a homogeneous solution is prepared, then polyethylene glycol or polyvinyl alcohol is added to aqueous solution with stirring at 4700 rpm and 70° C. for 18 hours to produce a target product (ref., for example, GB Patent 2214080, IPC A01 N 25/28, 1989). However, such method are regarded to be not effective enough for their being labour-consuming. In addition, these known methods for making microcapsules require use of toxic organic compounds.

The prior art also knows methods for the production of microcapsules to contain agents useful for killing household insects. Such known methods are based on the preparation of a composition comprising microcapsules containing a core of an active insecticidal material, wherein chlorpyrifos solution in organic solvent is used as said active insecticidal material, or a method of producing a freon-containing microcapsule. However, an insecticide solution is used in the former case, while the latter case is directed to making a thin shell which is fully collapsible when a microcapsule is heated.

The present invention offers a simplified method for making a micro-encapsulated solvent due to shorter synthesis time and making a microcapsule shell which is not collapsible in full when heated.

The above-mentioned method as per the present invention is realizable since the production of a microcapsule, which is based on preparing an aqueous suspension comprising microcapsules having an organic solvent core surrounded by a polymeric material shell, includes the step of adding polyisocyanate to the organic solvent to form microcapsules, followed by stirring the resultant solution in an aqueous dispersion medium comprising 0.5% of polyvinyl alcohol in distilled water for 5-20 min till the preparation of a micro-emulsion comprising particles of 5-500 μm in size, and further followed by adding continuously 10%—aqueous solution of polyethylenepolyamine at a slower stirring rate to form a microcapsule shell; wherein a ratio of polyisocyanate dissolved in the encapsulated solution to poly ethylenepolyamine being dissolved in the aqueous dispersion medium is 1:1.

The following chemicals are used for synthesizing of microcapsules:

Xylol (compliant with technical specifications TU 6-09-3825-88 rev. 1.2)

Colorless fluid; weight share of an active substance is at least 99.3 wt. %; density at 20° C. is 0.876-0.880 g/cm$^3$; temperature range for distillation at 760 torr to distillate at least 95 vol. % of the preparation is 143-145° C.; bromine number expressed in g of bromine per 100 g of the preparation is not more than 0.05; purification level as per reference scale is not more than 0.15; grease content level is not more than 10.

Butyl acetate is colorless clear fluid having characteristic odour (GOST 22300-76), weight content of active substance at least 98.3 wt. %; weight content of non-volatile substances is not more than 0.002 wt. %; weight content of acids (equivalent to acetic acid) is not more than 0.005 wt. %; weight content of water is not more than 0.1 wt. %.

Polyethylenepolyamine (PEPA) compliant with technical specifications TU 2413-357-00203447-99. Brown clear fluid; weight share of total nitrogen is 30; chlorine ions are not present; weight content of mineral impurities is 0.2; weight content of the fraction distilled under residual pressure of 1.3 kPa (10 mm Hg) within temperature limits:

0.75° C. not more than traces 1, 0.75° C. to 200° C. not more than 23.0;

weight content of still residue boiling above 200° C. ranges 65-75; weight content of tertiary amino groups ranges 5-9; weight content of water is not more than 2; weight content of nitrogen titrated by acid is 19.5-22.0%%; curability is not more than 1.5 hours.

Polyisocyanate is red-brown viscous fluid with crystallization temperature below 10° C.; $t_{boiling}$=400° C.; $d^{20}$–1.22–1.25; $t_{evaporation}$=185° C.

Polivinyl alcohol (complying with technical specifications TU 6-09-4004-67) is a thermoplastic material of microcrystalline structure, molar weight is 10,000-50,000; $t_{glass\ transition}$=57° C., density is 1.29 g/cm$^3$, $t_{decomposition}$=220-235° C. (without melting), dissolvable in hot water, resistant to oils and fats; dilutable in acids and alkali.

There are two phases of the production of microcontainers. The first phase includes production of microcapsules comprising an organic solvent using known method, then such microcapsules are used for production of microcontainers on the second phase.

EXAMPLE 1

Production of Microcapsules

Components to be prepared:

| | |
|---|---|
| 1. Solution (1) of polyisocyanate in xylol (or in butylacetate) having the concentration of 10% . . . | 200 g |
| 2. Solution (2) of polyvinyl alcohol in distilled water having the concentration of 0.5% . . . | 600 ml |
| 3. Distilled water to be used for dilution of the resultant stock . . . | 200 ml |
| 4. Polyisocyanate . . . | 20 g |
| 5. Solution (3) of polyethylenepolyamine in water having the concentration of 10% . . . | 15 ml |

First phase. Production of polyisocyanate solution emulsion and primary shells of microcapsules.

1. Polyisocyanate is solved in solution (1).
2. Solution (2) is poured into an emulsifier reactor, then stirring is performed using a stirrer at a medium rate and a retention is done for 5 minutes.
3. A thin jet of solution (1) is directed to the emulsifier reactor.
4. Stirring rate of the stirrer is increased till emulsion drops of required size are produced (monitoring of the mixture is performed by sampling system with microscopic analysis of samples thus obtained), said mixture is further retained under these conditions for at least 7 minutes till microscopic images start exhibiting a full stability during analysis.
5. Solution (3) is further added (for 20 minutes) to the mixture produced as described above.
6. Stirring rate of the stirrer is reduced to 25% of its maximal stirring rate and the mixture being stirred is retained for at least 10 minutes.

Second phase. Production of microcapsule shells.

7. Stirring is stopped and the resultant mixture is poured to receiver reactor containing 200 ml of water. Then, slow stirring is performed again with monitoring of the process for prevention of deposit formation and, afterwards, the stock thus produced (FIG. 1) is discharged to a storage tank.

In order to produce larger quantities of microcapsules, the first phase is performed for many times in a cyclic manner with discharging of a resultant product to the receiver reactor, wherein 200 ml of water is added whenever each first phase production cycle ends.

EXAMPLE 2

Manufacture of Microcontainers

Using decantation and vacuum filtration, an aqueous phase is removed from the suspension produced. Then, wet microcapsules are dried at 55-75° C. under appropriate drying flow conditions to gain a constant weight.

Dried microcapsules are placed to an oven operating at 200-300° C. to be held under these particular thermal condition with periodical stirring till gaining a constant weight. As a result, a solvent is removed from microcapsules, thus perforating (by means of solvent vapor breakthrough) their shell and forming microcontainers (FIGS. 2, 3, 4 and 8).

A size of holes perforated in the microcontainer by solvent vapor breakthrough from the inside of spherical microcapsules is defined by the following interdependent parameters:

1. Strength of microcapsule shell which is defined by shell thickness and microcapsule diameter, and also strength characteristics of shell material, i.e. chemical composition of a polymer.
2. Saturated vapor pressure of a solvent contained inside the microcapsule and a rate of saturated vapor pressure rise during heating of the microcapsule.

In case of having identical microcapsule diameter and identical shell thickness it is necessary to have high pressure of solvent saturated vapor and slow heating of the microcapsule in order to produce relatively small holes in the shell. Larger holes in the shell require lower pressure of solvent saturated vapor and slow heating of the microcapsule.

The same type of polymer (e.g. polyurea material) may be used for shell, but components of such polymer may vary. Any other polymers are fit as well. As a result, it is possible to vary value of saturated vapor pressure and value of a rate of saturated vapor pressure rise during heating of the microcapsule in order to make the desired size of holes.

If microcapsules made of polyurea having a certain composition are 50 μm in diameter and have the shell thickness of 0.5 μm, and when xylol is used as a solvent, heating of said microcapsules from room temperature to 240° C. for 5 minutes makes holes of 5 μm in diameter, while the same heating for 30 minutes makes holes of 15 μm in diameter.

Alteration of solely the polyurea composition results in formation of holes with quite other diameters at the end of the above-said heating operations. Likewise, use of other values of shell thickness produces holes of different sizes. A size of holes also depends on types of a polymer and a solvent to be used.

Therefore, when it comes to production of microcontainers, diameter of holes are defined in advance on the basis of the initial properties of microcapsules to be produced, such as strength of microcapsule shell and saturated vapor pressure, i.e. during synthesis of microcapsules when said diameter is present after being calculated. Furthermore, a prerequisite is hole diameter pre-selection that a hole cannot be greater than microcapsule diameter, and also that perforation of holes with a diameter lesser than that of fungal spores does not make sense. It is useless to have a microcontainer whose diameter is smaller than fungal spore diameter.

EXAMPLE 3

Production of a Biologically Active Agent 1 liter of a biologically active suspension provided in the form of fungal spores and a liquid phase is poured into a 2 liter vessel (FIG. 9) with a propeller blade stirrer capable of operating at a rate of 300-700 rmp.

Further, small portions of microcontainers amounting to 50 g are added to above-said vessel and a resultant mass is stirred for a period lasting 40-60 minutes. End point of adding fungal spores to microcontainers is detected by turbidity method when a constant optical density in liquid phase samples being taken is achieved. Microcontainers containing fungal spores placed inside are shown on FIGS. 5, 6, 7 and 10.

The next step is removing by decantation and vacuum filtration of the liquid phase from the produced suspension comprising microcontainers, then wet microcontainers containing fungal spores are subjected to drying at 25-45° C. under appropriate drying flow conditions until they gain a constant weight.

EXAMPLE 4

Comparative Tests of Anti-Locust Micro-Insecticidal Agents Provided in Various Preparative Forms An objective of these tests is to assess a dynamics of the mortality of the herding locusts infected with fungal infection depending on preparative forms of mycoinsecticides of anti-locust agents.

Studies were performed using the following preparative forms based on conidia *Beauveria bassiana* (Balsamo-Crivelh) Vuillemin:

1. Aqueous suspension.
2. Oil suspension.
3. Inventive microcontainer containing the above-said conidia.

Subjects exposed to such studies were locust larvae of different ages and imago of Asian locust and Italian locust. Untreated locust larvae were used for control.

The following treatment techniques were used for studies:

1. Applying a solution directly onto insect subject by hand-operated sprayer.
2. Treatment of foodstuffs.
3. Treatment of soil.

Experimental Methodology

Infection load was created such that a level of $7*10^{12}$ conidia per hectare could be achieved. For experiments, cages closed by fine mesh with dimensions 100×100×100 cm were used on open sites and shaded sites. In order to reduce the amounts of fungal conidial carried by the wind, such cages were separated by a windproof separating partition. Each cage was containing 20 insects. Weather conditions: average air temperature was 23-25° C. with maximal level of 36° C., soil temperature was 45° C., humidity was 49-56%, wind velocity was ranging from 5 to 15 m/s. Observation period duration was 30 days.

1. Treatment of Insect Subjects

Analysis of the mortality of the locust larvae as a result of using various preparative forms demonstrates the following results:

Shaded Sites

For all preparative forms, the mortality for insect subjects was 80-100% on $25^{th}$-$27^{th}$ day of experimentation (FIG. 11). It should be mentioned in this connection that an aqueous emulsion of bioinsecticide, as compared to an oil suspension and an suspension comprising microcontainers, is less effective in the course of time. Thus, 40% of insect subjects were killed on $14^{th}$-$16^{th}$ day as a result of use of the aqueous suspension, while in case of the treatment with oil suspension and suspension comprising microcontainers the same lethal effect was achieved on $8^{th}$-$9^{th}$ day (FIG. 11).

Open sites

Under conditions of intense solar radiation, the effectiveness of aqueous suspension carrying the bioinsecticide reduced by more than two times and the mortality of insect subjects was not more than 40-45% on $25^{th}$ day of experimentation (FIG. 12). The most probable explanation for this effect is that during initial 10-16 hours the fungus failed to penetrate inside insect's body as fungal conidia were killed by intense solar radiation. The second probable factor causing reduced effectiveness is that in view of poor adhesive properties fungal particles (drops of solution) tend to fall down from insect subject body leaving the insect alive. In the event of using oil suspensions, the effectiveness of mycoinsecticide reduced, on the average, to the level of mortality of 60-70% (FIG. 12). Such result relates to properties of oil protecting the insecticide from solar radiation and drying and improving the adhesive properties. The test results obtained are fully consistent with results of earlier experiments (Krukov V. Ju., Lednev G. R., Levchenko M. V., Jaroslavtseva O. N., Makarov E. N., Bimagambetov E. Zh., Duysembekov B. A., Glupov V. V., "The influence of fillers on biological effectiveness of conidial biomass of entomopathogenic fungus *Beauveria bassiana* used under the locust situation of Kazakhstan", J. Agrochemistry, 2010, No.12, p. 24-28.

In case of using a preparative form provided as a suspension comprising microcontainers, as compared to experimentation carried out on shaded sites, no fundamental differences were observed. The mortality of insect subjects on $25^{th}$ day of experiment was 85-100% (FIG. 12) owing to reliable protection of the microorganism held in the microcontainer from solar radiation and drying, and also due to high adhesive properties of walls of the microcontainer that enable such microcontainer to bind reliably within insect subject body.

2. Foodstuff Treatment

The treatment was performed by a hand-operated sprayer according to the following options:

Treatment immediately before placing the foodstuff to the cage with insect subjects;

Treatment of the foodstuff, followed by drying for several hours under natural conditions.

As compared to the treatment option comprising spraying mycoinsecticidal agent directly onto insect subjects, a common trend is a drop of the treated insect mortality by 15-20%.

Shaded Sites

Comparing the effectiveness of all three preparative options tested, it should mentioned that there is a general trend of reducing the treated insect mortality by 5-10% for suspensions and by 25% for aqueous solutions in the event of treating the foodstuff just before placing to cage with insect subjects, as opposed to direct treatment of insects under tests. In case of drying the foodstuff, the effectiveness of an aqueous solution is reduced by more than two times, providing for the mortality level of not more than 40-50% (FIG. 13) as compared to option of direct treatment of insect subject. The cause is that droplets of the solution tend to fall down from the leaves used as a foodstuff for insects and eventually dry. In the event of using oil suspension and emulsion comprising microcontainers the effectiveness of treated foodstuff does not reduce strongly and such effectiveness reducing is about 10% (FIG. 13).

Open Sites

The effectiveness of the first two preparative forms reduces remarkably as compared to experimentation on shaded sites. The more probable reason for that is greater solar activity and higher temperature assisting to quick drying of droplets of the solution. If during the several initial hours a bioinsectisidal agent fails to penetrate inside the insect along with the treated foodtuff or fails to be retained inside insect's body, an insecticidal action of said agent stops since it becomes dried. The mortality of insects is 40-55% for oil suspensions and about 30% for aqueous ones (FIG. 14). No remarkable effects are produced by higher temperature and stronger UV radiation upon a suspension comprising microcontainers and mortality of the insects is 75-80% (FIG. 14).

3. Soil Treatment

For experimentation, the following technique was used:

direct treatment of insect subjects just before placing to cage;

treatment of soil, retention for 36 hours on experimental site, followed by placing the locusts to cages.

In its turn, treatment of soil primarily contemplates a contact way of spreading the infection. Therefore, a period of effective action of the agent is particularly crucial.

Direct Treatment Prior to Infesting with Insects

Figure 15:
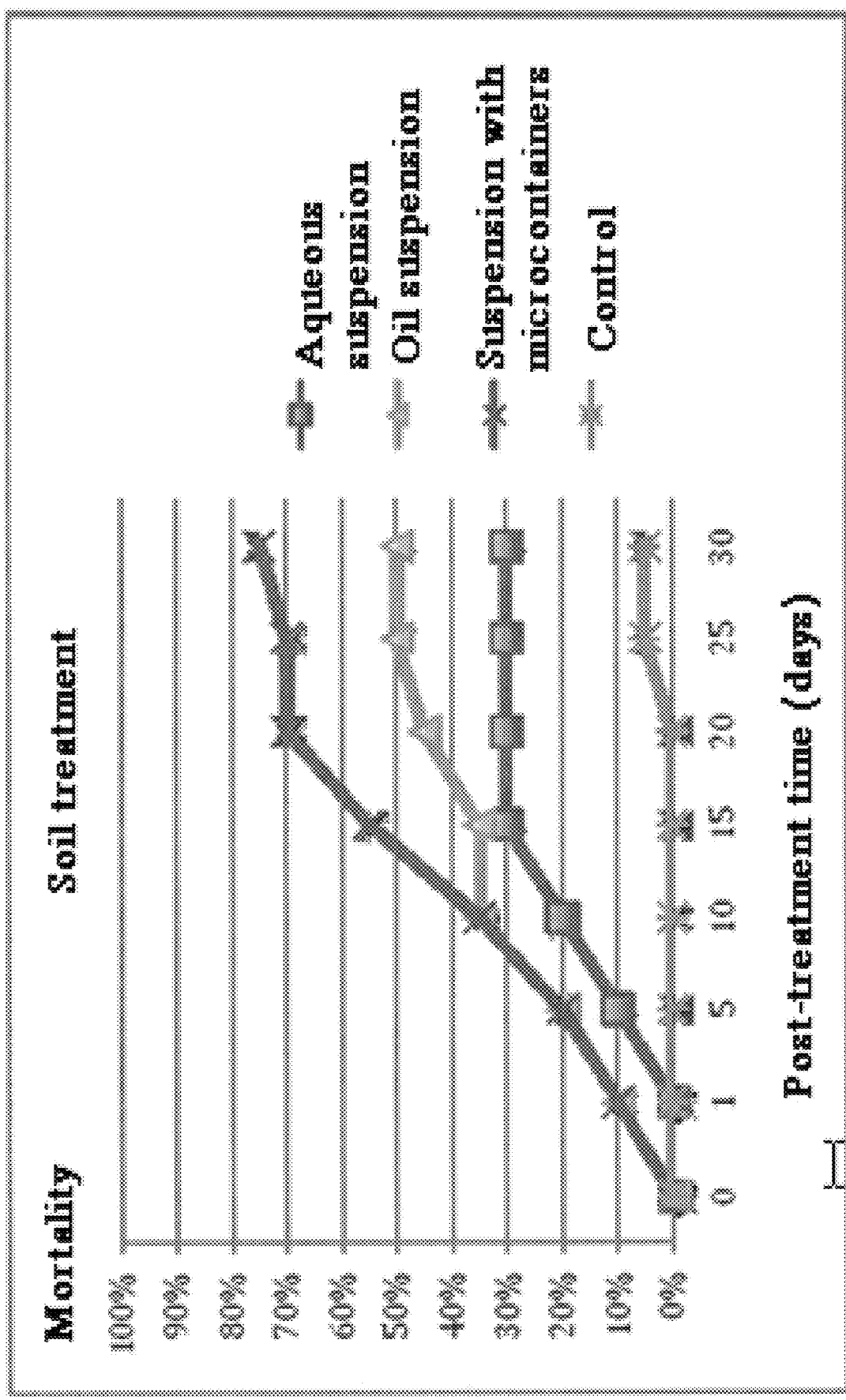
FIG. 15 shows a graph representing the mortality of locust larvae in case of using a mycoinsecticidal agent provided in various preparative forms. Preparative forms were used for the treatment of soil prior to being actually populated with insect pests.

The aqueous solution remains active for several hours, while a rate of effectiveness decreasing depends directly on soil temperature. Maximal mortality level for the locust subjects was about 30% (FIG. 15). The oil emulsion demonstrates better mortality level amounting to 50% (FIG. 15). The emulsion comprising microcontainers exhibits stable insecticidal properties such that the mortality of locust subjects was 70-75% (FIG. 15).

Soil Treatment with Retained Agent

Figure 16:
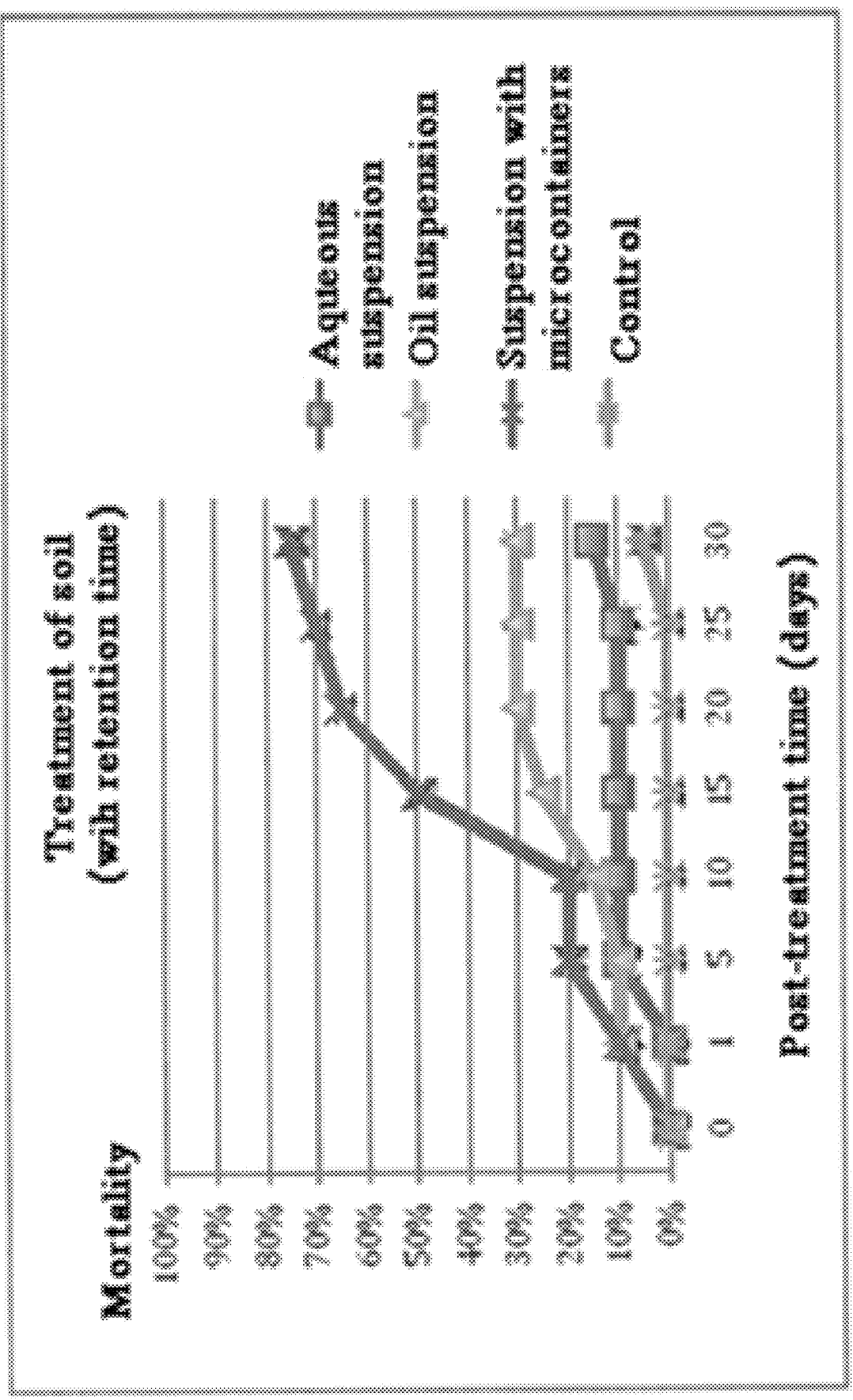
FIG. 16 shows a graph representing the mortality of locust larvae in case of using a mycoinsecticidal agent provided in various preparative forms. Preparative forms were used for the treatment of soil which was retained treated for a certain time prior to being actually populated with insect pests.

When it comes to the treatment the aqueous solution of the insecticidal agent, virtually no effectiveness was registered. It was lethal virtually for small amount of insect subject and no epidemiological peak was reached (FIG. 16).

Oil emulsions used at open sites proved to be ineffective because of solution drying. When used at shaded sites, a part of the solution remains active and capable of infecting the locust subjects. As a result, the mortality level was 30-35% (FIG. 16).

In the event of using an emulsion comprising microcontainers, the effectiveness of the agent being tested remains virtually unchanged. The reason for this phenomenon is that walls of the microcontainer reliably protect microorganisms from harmful influence of negative factors and a fluid trapped inside the microcontainer does not block a growth of microorganisms and their passing through holes of pre-defined size to a surface of the microcontainer. In case of elimination of a surface layer, there is a replacement of the eliminated layer with a new and highly active layer. The mortality level of the locust subjects in the event of using an emulsion comprising microcontainers is rather high and amounts to 70-75% (FIG. 16).

CONCLUSIONS

Testing of three preparative forms of bioinsecticidal agent demonstrates that a preparative form which is most resistant to unfavourable environmental effects is an emulsion comprising microcontainers. It has a long exposition allowing its use as a barrier to struggle with the locust pests. Wide temperature range and resistance to UV radiation open up the possibility of use in various climatic zones.

INDUSTRIAL APPLICABILITY

Up-to-date methods, technologies and materials also provide for an actual possibility for realization of the above-described inventive subjects-matters. The above-referenced examples are supportive to such conclusion. Industrial applicability of the above-said inventive subjects-matter will be found indisputable by those skilled in the field of the protection of crops against insect pests and operating both in scientific research, and agriculture, gardening and forestry.

The invention claimed is:

1. A method for producing a biologically active agent for crop protection against insect pests, the method comprising:
   providing microcapsules comprising a polymeric material shell and an organic solvent core, and heating the microcapsules up to 300° C. to cause perforation of the microcapsule shell and formation of at least one hole in the shell by an action of a solvent vapor pressure of the core, and adjusting a size of the at least one microcapsule shell hole by selecting a proportion of polymeric material components for the shell and varying the solvent vapor pressure, thereby producing microcontainers;
   introducing a biologically active suspension comprising entomopathogenic fungal spores and a liquid phase into the microcontainers, wherein the microcontainers are hollow receptacles each having the polymeric material shell and the at least one hole to receive the spores;
   decanting the liquid phase; and
   drying the microcontainers comprising entomopathogenic fungal spores.

2. The method of claim 1, wherein the entomopathogenic fungus is selected from the group consisting of fungal species *Beauveria bassiana, Pandora neoaphidis, Entomophaga maimaiga, Metharhizium anisopliae* var. *acridium* and *Metharhizium anisopliae* var. *anisopliae*.

3. The method of claim 1, wherein the entomopathogenic fungus is *Metharhizium anisopliae* var. *acridium* species of entomopathogenic fungus.

4. The method of claim 1, wherein from 1 to 100 of fungal spores are introduced into each microcontainer.

5. A biologically active agent, produced by the method of claim 1.

6. The method of claim 1, wherein a diameter of a microcontainer is from 5 to 500 μm.

7. The method of claim 1, wherein a shell thickness is from 0.05 to 5 μm.

8. The method of claim 1, wherein a diameter of the at least one hole is at least 5 μm.

9. The method of claim 1, wherein the drying the microcontainers comprising entomopathogenic fungal spores is performed at a temperature of from 25 to 45° C. under flow-through conditions until a constant weight has been achieved.

* * * * *